(12) United States Patent
Roland et al.

(10) Patent No.: US 6,444,473 B1
(45) Date of Patent: Sep. 3, 2002

(54) ATMOSPHERIC OZONE CONCENTRATION DETECTOR

(75) Inventors: Charles M. Roland, Waldorf, MD (US); Peter H. Mott, Washington, DC (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/275,272

(22) Filed: Mar. 23, 1999

Related U.S. Application Data

(63) Continuation-in-part of application No. 08/625,506, filed on Mar. 29, 1996, now Pat. No. 5,972,714.

(51) Int. Cl.$^7$ .......................... G01N 17/00; G01N 21/77
(52) U.S. Cl. ................. 436/135; 73/31.02; 116/202; 116/212; 356/433; 422/58; 422/82.05; 422/87; 436/164
(58) Field of Search ............................... 422/55, 58, 61, 422/82.05, 86, 97, 91, 99, 104; 436/135, 164; 73/31.02, 31.03, 23.2; 356/300, 445; 116/206, 212, 278

(56) References Cited

PUBLICATIONS

Serrano et al., Atmos. Environ., Part A (1993), 27A(3), pp. 431–442.*
Hong et al., Polym. Degrad. Stab. (1995), 49(3), pp. 437–447.*
Chemical Abstract No. 130:169331, Eng et al., J. Rubber Res. (Kuala Lumpur) (1998), 1(3), pp. 133–145.*

* cited by examiner

*Primary Examiner*—Jan Ludlow
(74) *Attorney, Agent, or Firm*—John J. Karasek; George A. Kap

(57) ABSTRACT

An ozone detector in the form of two basic embodiments which can measure ozone concentration in ambient air at 0.001–1 ppm. The first embodiment includes a stretched elastic material and a standard which can give ozone concentration in response to degree of microcracking or frosting of the elastic material. The second embodiment includes a chamber containing a long strip of elastic material, a component for stretching the material, a light source for generating a light and illuminating the film and a detector for detecting reflected, transmitted through or scattered light by the material.

20 Claims, 7 Drawing Sheets

ATMOSPHERIC OZONE CONCENTRATION DETECTOR

CROSS-REFERENCE TO RELATED APPLICATION

This is a continuation-in-part application of application NC 77,117 bearing Ser. No. 08/625,506 entitled "Atmospheric Ozone Concentration Detector" which was filed Mar. 29, 1996, now U.S. Pat. No. 5,972,714 and which is herein incorporated by reference.

BACKGROUND OF THE INVENTION

1. Field of Invention

This invention pertains to measurement of ozone.

2. Description of the Related Art

Ozone is deleterious to materials and to humans. OSHA's limits for average ozone concentration are up to 0.1 ppm over 8 hours or up to 0.3 ppm over 15 minutes.

Presently, there are a number of techniques for measuring atmospheric ozone concentration. One technique employs ultraviolet light absorption whereas another employs the differential creep of rubber technique.

The technique of ultraviolet light absorption takes advantage of a 254 nm absorption line of ozone in the electromagnetic spectra and thus measures the concentration of ozone directly. Here, a measured sample of air is pumped into a chamber and illuminated at one end with a low pressure cold cathode mercury vapor ultraviolet light. The ultraviolet light from the mercury lamp has emission at 254 nm. At the opposite end of the chamber is a cesium telluride vacuum diode detector. The determination of ozone is carried out in two steps. Initially, an ozone-free reference gas sample is pumped into the chamber and the transmitted light intensity is measured. Any ozone present in the reference gas is rapidly destroyed by passing the gas over manganese dioxide. In the second step, an "ozone gas sample" is pumped into the same chamber and the transmitted light is measured. The ozone concentration in the "ozone gas sample" can be easily determined by application of a formula.

Ozone detectors which operate on the basis of ultraviolet light absorption can detect as little as about 0.001 ppm of ozone but have the disadvantage of being somewhat large at about 19"×12"×6.5"; of being heavy at about 22 pounds; of requiring a full line voltage of 115V; of requiring a warmup time of about 2 hours; of being expensive at about $4,500–$12,000 per detector; and of requiring to be stationary. In short, such detectors are sensitive, expensive and are intended for stationary laboratory use.

The fact that a detector must remain in the lab is a serious disadvantage because ozone concentration often needs to be measured in widely separated locations, such as when one is determining the average ozone concentration over an entire city or when one needs to measure the ambient ozone in every room in a building. Furthermore, another critical disadvantage of an absorption ozone detector resides in the fact that ozone is very chemically active and thus easily destroyed inside many containers, which precludes sample collection.

In a differential creep of rubber technique, a standard rubber thread is divided in half, one part is exposed to the atmospheric ozone whereas, the other part is protected from ozone. The unexposed portion creeps at a lower rate than the exposed portion and pulls an indicating needle attached to the exposed rubber along a scale, thus giving a measure of ozone concentration.

SUMMARY OF THE INVENTION

An object of this invention is an apparatus for measuring ozone.

Another object of this invention is a quick measurement of ozone in atmosphere by means of a stretched elastomer which frosts over in response to microcracks created in the elastomer by ozone in the atmosphere.

Another object of this invention is a highly practical and a highly sensitive electrical measurement of light intensity from a frosted elastomer adjusted for light intensity from unfrosted elastomer.

Another object of this invention is a device for providing rudimentary "go-no go" ozone concentration results.

These and other objects of this invention are realized by a structure characterized by a stretched or stressed elastic material which becomes whitened or frosted or transluscent when ozone in the surrounding air contacts it and creates microcracks therein which scatter light.

BRIEF DESCRIPTION OF THE DRAWING

For a better understanding of these and other objects of the present invention, reference herein is to the following detailed description of the invention which is to be read in conjunction with the accompanying drawings, wherein.

DETAILED DESCRIPTION OF THE INVENTION

The subject matter herein is directed to measurement of ozone by means of a stretched elastic material which frosts when exposed to ozone. The ozone detector that measures ozone concentration in the surrounding environment operates on the principle of ozone creating a multitude of microcracks in the stretched elastic material.

Cracks produced in an elastic material by ozone extend generally perpendicularly to the direction of the stretching force. The cracks are on the order of 1 micron to 1 mm long and about 1 mm or less in width. Length of the cracks is variable and increases with ozone concentration and duration of exposure whereas the crack width remains essentially unchanged.

Stress or strain has two effects on the ozone-induced cracking of stretched rubber. Below a certain threshold strain of about 1 or 2%, no ozone cracking takes place. Beyond this minimum threshold, the sensitivity to ozone-induced frosting increases with increasing strain. Hence, the concentration of cracks increases so that higher strains accelerate development of opacity. In using a stretched rubber to detect ozone, higher strains confer higher sensitivity, and thus the ability to detect low levels of ozone at shorter times. Lower strains reduce the sensitivity, and thus increase the working time, whereby ozone can be detected.

Figure 8:
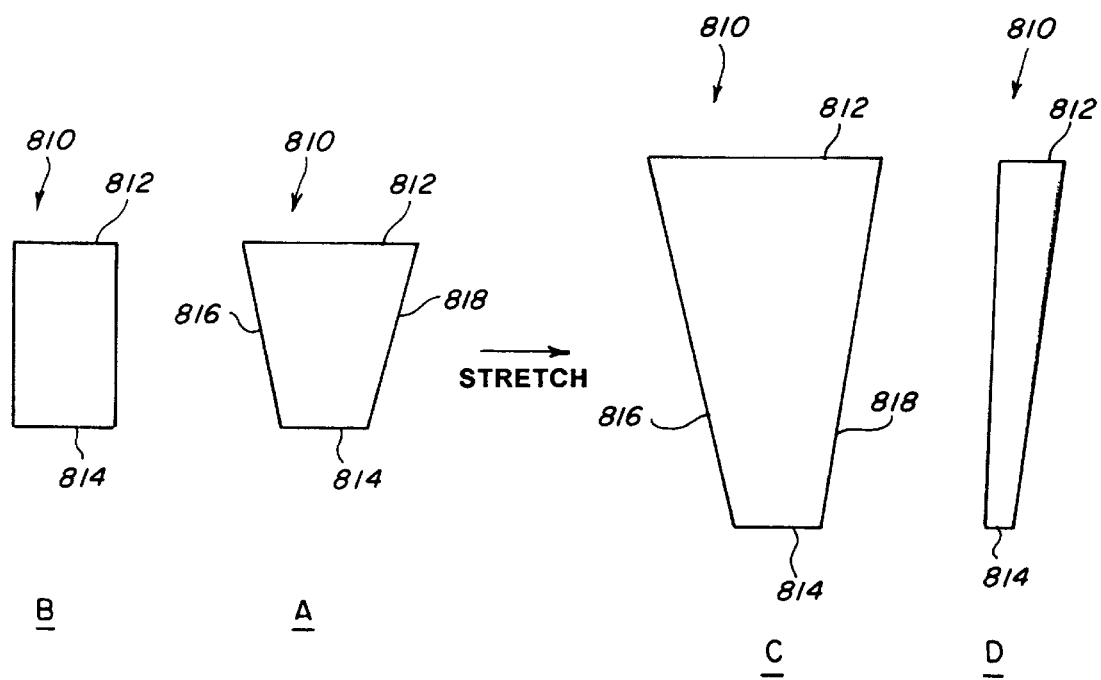
FIG. 8 is an illustration of a trapezoidal rubber sample of uniform thickness but having non-uniform cross-sectional area which is stretched and then exposed to an ozone-containing air sample.

An entire range of sensitivities can be obtained by using elastic material with a non-uniform cross-sectional area. The ends of an elastic material of variable thickness are displaced a distance corresponding to some average strain, as shown in FIG. 8. Since the force along the stretched direction is constant, the stress, which is equal to the ratio of the force to the cross-sectional area, varies from the top, where it is a minimum, to the bottom, where it is maximum. The strain, to a very good approximation, is proportional to the stress, so that the strain also varies from some minimum to some maximum value. The low strain end of the sample is below the threshold strain for ozone cracking. As a consequence of the geometrically-induced distribution of strains, the ozone response varies from zero at the top, where the cross-sectional area is thickest, to very high at the bottom, where it is thinnest. Opacity will develop initially at the bottom, and over time propagate upwards. It will stop when the strain falls below the minimum necessary to induce ozone stress cracking. Through the use of a predetermined calibration, the measurement of opacity or its reciprocal, i.e., light transmission, at any position provides a measure of the atmospheric ozone concentrations.

In the first or the "go-no go" embodiment, an elastic film is stretched on a frame and the stretched film is exposed to ozone-containing environment which causes microcracks. The microcracks appear to the casual observer as "frosting" in which the elastic material is transformed from clear to transluscent. The frosted film is then compared to a standard to determine the ozone concentration.

In the second embodiment, light is projected onto a stretched elastic material disposed in an ozone-containing environment and its scattered or reflected intensity is measured on the opposite side or on the same side. This intensity is compared to a base intensity, then converted to an electrical signal and the relative intensity is then calculated. The relative intensity is then converted to a read-out of actual ozone concentration in the surrounding atmosphere.

The elastic material used in the first or the second embodiments, or any embodiment of this invention, can have a uniform or non-uniform thickness or cross-sectional area.

Figure 1:
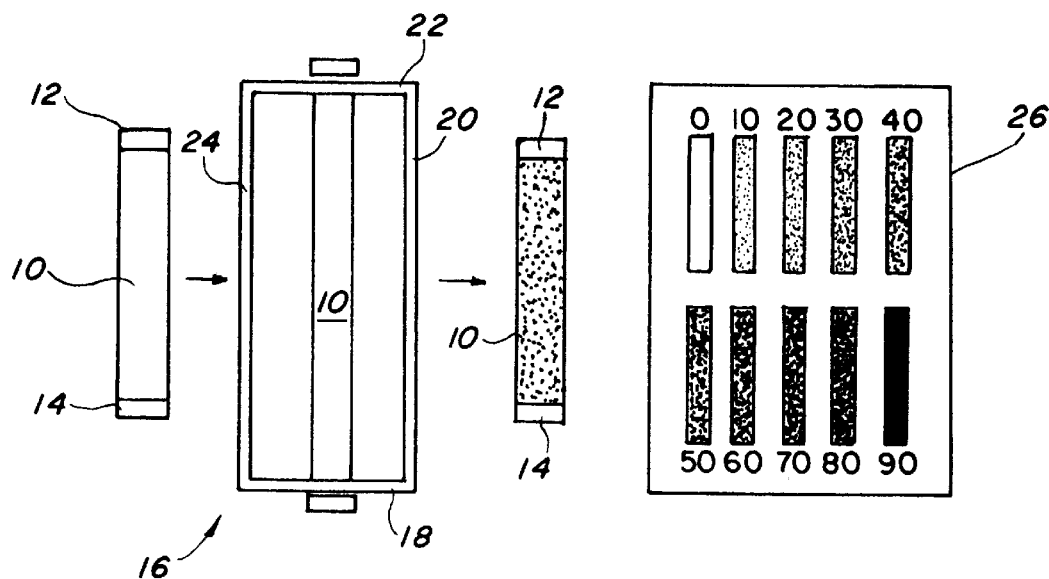
FIG. 1 is a front elevation view of the go-no go ozone detector showing an elastomeric material which is stretched in an environment containing ozone to produce a degree of frosting which is compared to a standard.

The first embodiment, which can measure ozone concentration from a low of about 1 ppb to a high of about 500 ppb, is illustrated in FIG. 1. This embodiment is also referred to herein as "go-no go" since it can give ozone concentration quickly in a matter of a few minutes or less. In this embodiment, elastic material 10 is secured at both ends to holders 12, 14 and then stretched on frame 16 which is rectangular and consists of rigid members 18, 20, 22, 24.

The frame can be of any suitable form. In operative condition, holders 12, 14, are disposed respectively on frame members 18 and 22 and elastic material 10 is stretched between members 18, 22 since the distance between members 18, 22 is greater than the length of material 10 in its unstretched condition. The length of the frame can be changed to provide for different stress in the elastic material in order to adjust the ozone sensitivity. The ozone sensitivity can be increased by stretching the elastic material to a greater degree.

The material stretched on the frame secured to holders 12, 14 at opposite ends thereof is placed in ozone-containing environment for a predetermined period of time to allow ozone to attack it and to develop microcracks therein which results in a frosted material. The frosted material 10 is compared to a standard 26 that can be in the form of a card containing a series of indicia marked 0, 10, 20, 40 and so on of different intensity of frosting, with darker colors corresponding to greater concentrations of ozone in the atmosphere.

The embodiment illustrated in FIG. 1 is suitable for measuring concentration of ozone at many locations along a highway, over a city or at any other location. This embodiment can quickly give a measurement in any location far away from a laboratory.

Figure 2:
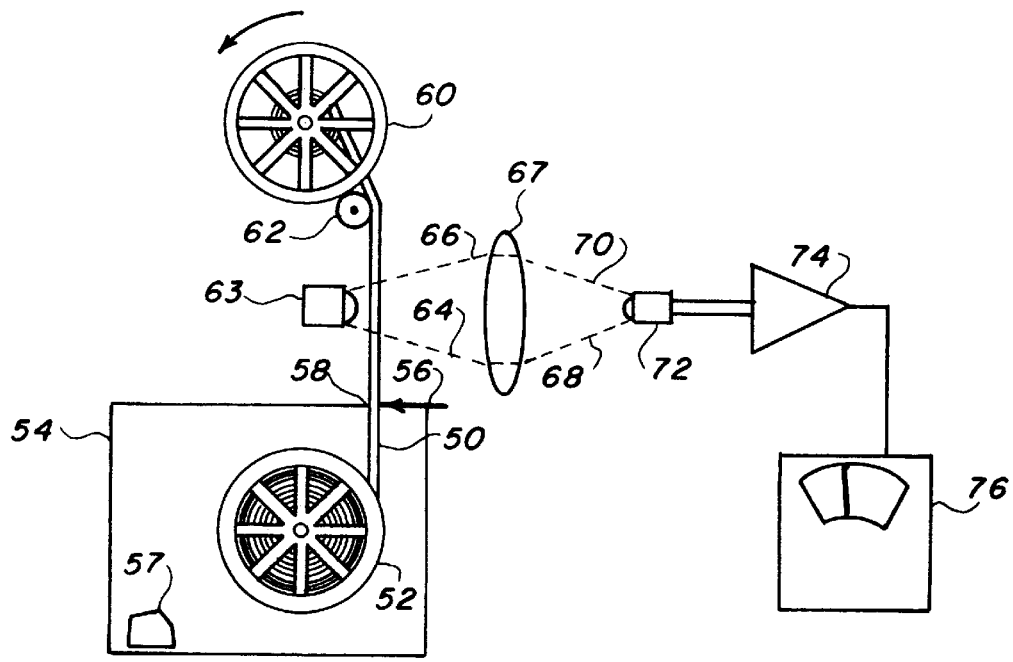
FIG. 2 is a front elevation of an ozone detector containing a light source, an extended elastic material and means for detecting light intensity of light reflected from the material and converting it to an electrical value.

FIG. 2 illustrates the second embodiment of ozone determination which can routinely measure ozone concentration. There is no fundamental limitation on the range of ozone concentration, measurable with this embodiment, however, for purposes of specificity, this embodiment can measure ozone concentration, from a low of about 1 ppb to a high of about 1000 ppb. The measurable zone concentration can be further extended by modifications in the elastic material, number of the elastic material layers, intensity of the light, sensitivity of the detector and other parameters that should be obvious to a person skilled in the art.

In the second embodiment, elastic material 50 is rolled up on spool 52 in airtight chamber 54 where substance 56, such as manganese dioxide, may be included in the chamber to neutralize deleterious effects of ozone on the material. Airtight condition of chamber 54 can be assured by providing clamp 56 which provides an airtight seal at opening 58 through which material 50 exits chamber 54. In this arrangement, material 50 is clamped against the chamber walls to give an airtight seal around opening 58 and substance 57 is present in chamber 54 to prevent ozone from attacking the material. Therefore, material 50 in chamber 54 should be free of frosting due to ozone.

Material 50 is drawn from chamber 54 through opening 58 onto take-up roll 60 directly above spool 52 and spaced therefrom. A predetermined and adjustable tension is applied to the material by means of calibrated spring acting on the take-up roll 60. Auxiliary off-set pulley 62, riding on the periphery of take-up roll 60, can also provide sufficient tension in the material. A minimum tension in the material is necessary in order to determine ozone concentration in the surrounding gaseous atmosphere. The minimum tension required in the material in order to develop at least some frosting therein will depend on many parameters such as the type of polymer material used and stiffness of the polymer. However, such ,minimum tension contemplated herein is typically at least about 5 kPa, more often at least about 50 kPa.

At some convenient point between spool 52 and take-up roll 60, but typically close to opening 58 in order to avoid exposing material 50 to an atmosphere containing ozone, light source 63 is positioned close to the material. Any light source may be used. Typically, the light source is a light emitting diode (LED) or a laser. A lens, not shown, can be interposed between the light source and the material to enlarge diameter of the light impinging on the material. The light emitted by light source 63 is defined by diverging lines 64, 66 which impinge on converging lens 67 and exits lens 67 as light defined by converging lines 68, 70.

Light emitted by light source 63 before passing through the material 50 has intensity $I_0$ which is greater than transmission intensity I of the light after passing through the material. Depending on amount of ozone in the air surrounding embodiment of FIG. 2, the material will be frosted with microcracks therein which will scatter or diffuse light passing through the material. With greater concentration of ozone in the surrounding air, the elastomer will be even more frosted and intensity of the light transmitted through the material will be lower. Therefore, greater concentration of ozone in the surrounding air will create more microcracks in the material or a greater degree of frosting which in turn, will reduce intensity of the light passing through the material exposed to the ozone-containing atmosphere. Thus, intensity of light passing through the material is proportional to frosting of the material which is proportional to the quantity of ozone in the surrounding air. By detecting intensity of the light passing through the material, it is possible to correlate quantity of ozone in the surrounding air with the intensity of the light passing through the material.

In FIG. 2 light detector 72 measures light intensity of the light passing, through the material which is then compared to base intensity and the difference converted to a current. The current is then amplified in amplifier 74 and then converted to a voltage and read as voltage by means of voltmeter 76, as desired, and finally correlated to ozone concentration in the surrounding air.

The embodiment of FIG. 2 is operated by drawing a fresh material from the spool between the light source and the light detector and applying tension so that the material is stretched. Immediately before or after drawing the material and before ozone is allowed to create surface cracks therein, a baseline transmitted light intensity $I_0$ is measured by passing light through the stretched material. The material is then exposed to the ozone-containing atmosphere for a given length of time, which will depend on the ozone concentration and other circumstances. The transmitted light intensity I is measured once again. Alternatively, the rate of change of the ozone concentration can then be readily determined from the ratio $I/I_0$ or the rate of change of $I/I_0$ by means of a calibration.

Figure 7:
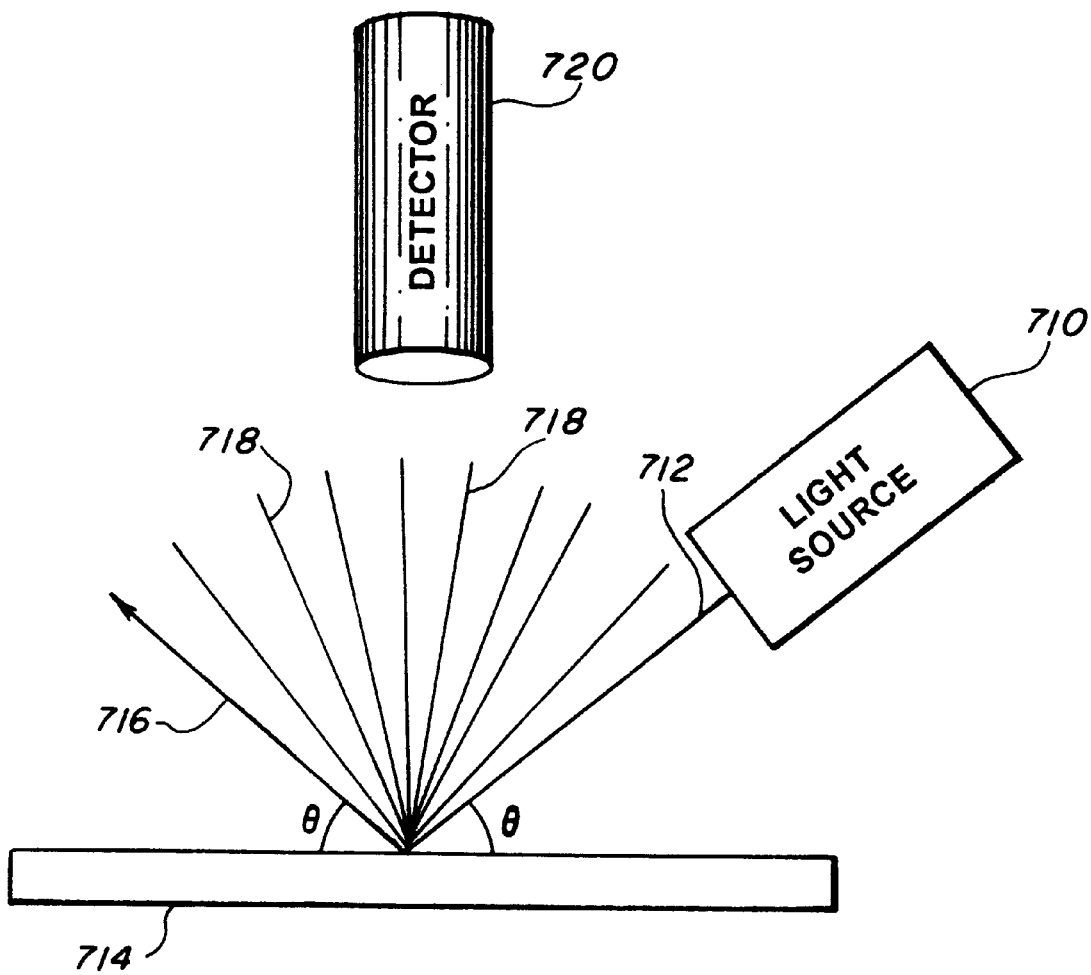
FIG. 7 shows measurement of backscattered light resulting from directing light at a stretched elastic material exposed to ozone-containing air.

FIG. 7 shows light source 710 producing light 712 of certain intensity impinging on sample of horizontally disposed elastic material 714 at about the angle of θ. Incident light 712 reflects light 716 from the material and backscatters at an angle to the material scattered light 718. Intensity of reflected light 716 is smaller than intensity of light 712 and intensity of backscattered light 718 is also smaller than intensity of light 712. Light detector 720, disposed on the same side of the material as light source 710, can be made to sense integral light intensity backscattered, or reflected light 718. Integral light intensity is the cumulative number of photons scattered or reflected from an area of the sample and collected over a finite angular range for detection.

Referring specifically to FIG. 8 shows a piece of rubber elastic material 810 having uniform thickness but non-uniform cross-sectional area that is stretched. The rubber piece 810 is shown in front view "A" as a trapezoid having upper edge 812, lower edge 814, and two side edges 816, 818. Upper edge 812 is longer than lower edge 814 and the two side edges 816, 818 are of equal length, although they, can be of different length. The upper and lower edges can be parallel to each other but they need not be. As shown in view "B" of FIG. 8, thickness of rubber piece 810 is uniform, although it can be variable. The edges are shown as being straight, although the edges can be of a different shape.

For determination of presence of ozone or ozone concentration, upper and lower edges 812 and 814 are clamped and the rubber piece 810 is stretched by drawing the clamps further away from each other to impart stress to the rubber piece 810. As stretching proceeds, rubber piece 810 becomes distended and since upper edge thereof is longer than its lower edge, the rubber piece becomes thinner at the bottom than at the top. View "C" of FIG. 8, is the front view of the rubber piece 810 after stretching and view "B" is its side view. As shown in view "C", rubber piece 810 has retained its general form after stretching although distended, with upper edge 812 generally parallel to lower edge 814, and side edges 816, 818 generally of equal length. As shown in view "D" of FIG. 8, rubber piece 810 is non-uniformly stretched least at the top, intermediate at about the middle, and most at the bottom. Stretching of rubber piece 810 is inversely proportional to the cross-sectional area thereof—with the largest cross-sectional area at the top of the rubber piece, intermediate cross-sectional area at about the middle, and the smallest cross-sectional area at the bottom.

View "B" of FIG. 8 shows uniform thickness of the rubber piece before it is stretched whereas view "D" of FIG. 8 shows a non-uniform thickness of the rubber piece after stretching being thicker at the top and thinner at the bottom. Generally speaking, thickness of rubber piece 810 in view "B" of FIG. 8 is thicker than that of rubber piece 810 in view "D" of FIG. 8. Initial thickness of the rubber piece before stretching can be made to be variable, as desired.

The embodiment illustrated in FIG. 8 has particular utility in situations where ozone concentration in a space is not known and it is desired to use an elastic material sample of varying thickness after distention varying from thinnest to thickest.

Selection of a suitable elastic material is made on the basis of whether ozone deleteriously affects any physical property thereof which results from chain scission caused by ozone attack on the material. This can be determined by measuring a physical property of the material, such as stiffness, before and after exposure thereof to ozone. Suitable material is cross-linked and flexible and can be stretched on application of a force thereto and elongated. Upon removal of the force which stretches the material, the material returns to a position which can coincide with its original extent or only part way. The term "elastic material" need not conform to the classical definition of an "elastomer" although it can. A classical definition of the term "elastomer" is any substance having properties of natural, reclaimed, vulcanized or synthetic rubber that stretches markedly under tension, has a high tensile strength in excess of about 5000 g/cm$^2$, retracts rapidly, and recovers most of its original dimensions.

Typical elastomers that are believed to be suitable herein include polyisoprene, polychloroprene, polybutadiene, styrene-butadiene, butyl rubber, nitrile rubber, ethylene-propylene-diene copolymers, and many others. Since ozone can attack both saturated and unsaturated bonds and cause chain scission, suitable elastomers need not contain unsaturation. For high ozone sensitivity, unsaturated elastomers are preferred.

Different elastomers are known to have different ozone concentration sensitivity. Typical elastomers suitable herein are those materials which are classical elastomers, preferably natural and synthetic rubbers which are characterized by presence of unsaturation, and especially polybutadiene or natural rubber, which have good ozone sensitivity. This means that stretched polybutadiene and natural rubber readily frost when exposed to an atmosphere containing ozone.

Thickness of the elastic material is only relevant in the context of extensibility thereof and passage of light therethrough. Based on practical considerations, thickness of a material either to be used in first or second embodiments, or in another embodiment based on the principles disclosed herein, is typically less than about 10 mm, more typically in the approximate range of 0.03–2 mm. With multiple layers of the material, substantially thinner than 0.03 mm films of the material can be used.

The elastic material is typically optically clear and has little absorbance of less than about 10%. As more colorant, such as carbon, is used in the elastic material, its absorbance increases and light transmission decreases. As little as a few percent of carbon additive in the elastic material can render the elastic material non-transparent to light.

Stretching of the material is prerequisite to the proper determination of ozone concentration in air. There is a certain minimum tension below which the material will not frost when exposed to any ozone concentration, even a high ozone concentration, such as about 0.5 ppm. This minimum tension is different for different materials. For polybutadiene, a useful minimum strain is believed to be about 2% and for natural rubber it is believed to be about 4%. At the opposite end, the maximum limit is that extension which will result in failure or rupture of the material. Therefore, the material can be stretched between these limits, bearing in mind that a more highly stretched material will generally be more sensitive. Typically, during the course of ozone determination as disclosed herein, the stress of the material will typically be, in the approximate range of 10–5,000 kPa, more typically 50–2,000 kPa.

The method for detecting ozone concentration comprises the steps of stretching an elastic material; impinging a gaseous mixture containing ozone upon the material and allowing frosting of the material to take place based on formation of microcracks due to ozone in the gaseous mixture; and detecting ozone concentration in the gaseous mixture by means of light transmission through the microcracked elastic material or reflected light from the elastic material or scattered light, based on degree of frosting of the material which is directly related to the ozone concentration in the gaseous mixture. The step of impinging light through the gas mixture containing ozone is accomplished by projecting a light beam therethrough emanating from a light source at the material.

Having described the invention, the following examples are given as particular embodiments thereof and to demonstrate the practice and advantages thereof. It is understood that the examples are given by way of illustration and are not intended to limit the specification or the claims in any manner.

EXAMPLE 1

This example demonstrates the use of elastic material of a uniform cross-sectional area and of a uniform thickness before stretching to determine ozone concentration.

The elastic material samples used herein were Goodyear Tire and Rubber type 1209 polymeric 1,4—polybutadiene mixed with dicumyl peroxide crosslinking agent prepared by compression molding for 30 minutes at 160° C. Samples I were prepared with 0.50 parts dicumyl peroxide per 100 parts of rubber (phr) and samples II were prepared with 0.94 phr dicumyl peroxide and therefore, were much stiffer than samples I. The sample films were 65 mm×13 mm×1.6 mm.

Figure 3:
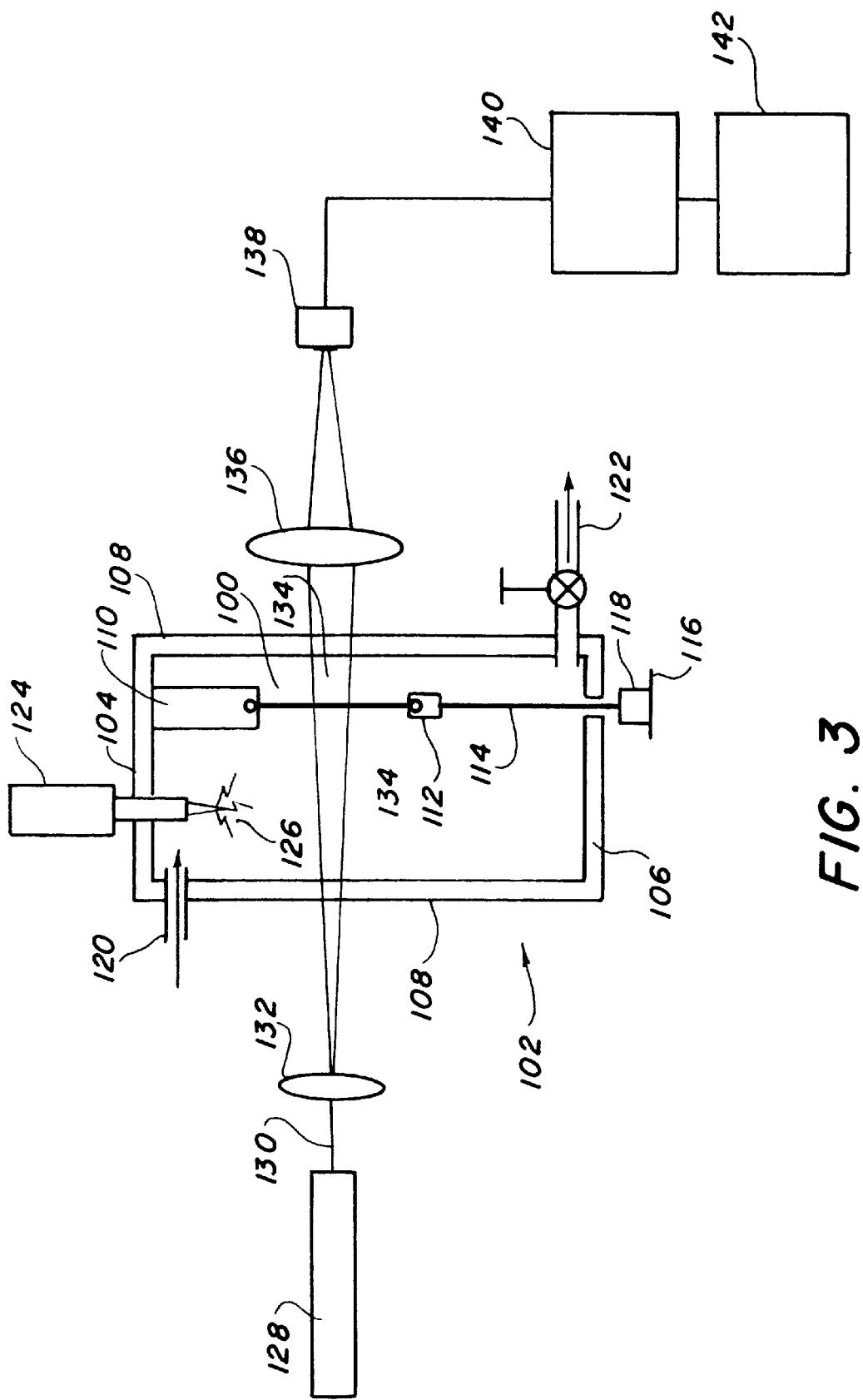
FIG. 3 is a schematic of experimental set-up which was used to obtain data on elastic material samples.

FIG. 3 shows a schematic of the experimental apparatus used to obtain the data herein. Each sample 100 was mounted in environmental chamber 102 made from 12 mm uniformly thick sheets of clear poly methyl methacrylate. Chamber 102 consisted of top panel 104, bottom panel 106, and side panels 108. The chamber measured about 17 cm×17 cm×36 cm. Sample 100 was clipped at its upper end to a rigid bar 110 and at is lower end to a clip 112 which in turn was connected to a wire 114 and that in turn was connected to a ring-like holder 116 on which were placed weights 118. The weights were varied as desired. Ambient room air was admitted into chamber 102 through entry port 120 at the top of the chamber and ozone was measured by taking air sample from the chamber through exit port 122 located at the bottom of the chamber. Measurement of ozone was made by drawing a known volume of air from chamber 102 through exit port 122 and through Drager tubes (not shown) available from National Drager, Inc., as item No. 6733181, with a calibrated hand pump (not shown), also available from National Drager, Inc., as model 31. For lowest concentrations of ozone in the chamber, sensitivity of the Drager tubes was increased by increasing the pumped volume of air.

The Tesla coil 124 was actuated periodically to produce sparks 126 which produced ozone in chamber 102. Increasing frequency of sparks 126 increased ozone concentration of ozone in the chamber whereas decreasing frequency of sparking had the opposite effect. One-half hour was allowed for ozone concentration to reach equilibrium after frequency of sparking was changed although ozone reading showed essentially constant value after only the first 10 minutes. During the equilibration period before the sample was stressed, intensity of light passing through the sample was monitored until no change was observed.

The light source was Uniphase 1104 HeNe laser 128 which produced a light beam 130 of 632.8 nm wavelength which was passed through spreading lens 132 positioned in front of the light source. The purpose of lens 132 was to spread or enlarge diameter of the light beam 130 emanating from light source 128 to where the beam diameter 134 on sample 100 was 1 cm. Scattering of the light through the walls of the chamber was negligible. The light beam 130 from the light source passed through spreading lens 132, through chamber sidewall 108, through film sample 100, through the opposite chamber sidewall 108, through converging lens 136 and into light detector 138 which was a photodiode detector UV100 from EG & G Inc. Current from the light beam entering light detector 138 was amplified by current amplifier 140 and the transmitted light intensity of the light beam passing through the film sample was obtained from voltmeter 142.

Just before sample 100 was stretched in chamber 102, a baseline light intensity was recorded. The relative high transmittance through the sample reported herein was determined by dividing the measured intensity by the baseline intensity.

After the ozone concentration in chamber 102 reached equilibrium after one-half hour of steady state operation, the sample was stressed by placing calibrated weights 118 on holder 116 and immediately initial light intensity was recorded followed by light intensity recordation thereafter at 30 second intervals. Because the samples had many inhomogeneities that scatter light, such as trapped dust particles, the initial relative transmitted intensity of the sample was usually different from the unstretched sample. The inhomogeneities in the samples increased noise of the experiment which was reduced by lens 132. Lens 132 increased the illuminated area and thus averaged out the inhomogeneities. It is estimated that the inhomogeneities contributed an error of about 5% in the value of the transmitted light.

Figure 4:
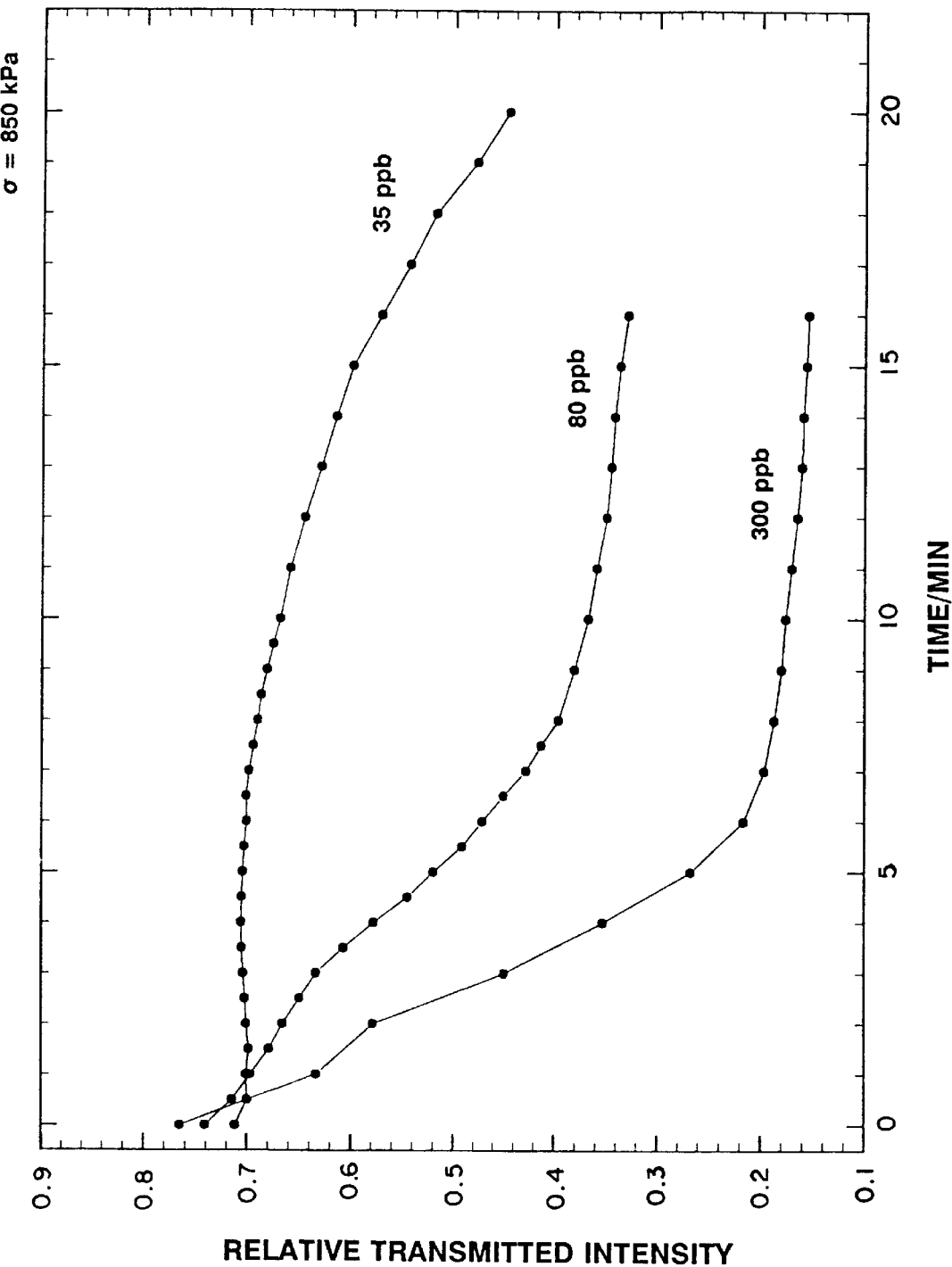
FIG. 4 is a graph of relative transmitted light intensity through elastic films versus time at constant tensile stress for three ozone concentrations.
Figure 5:
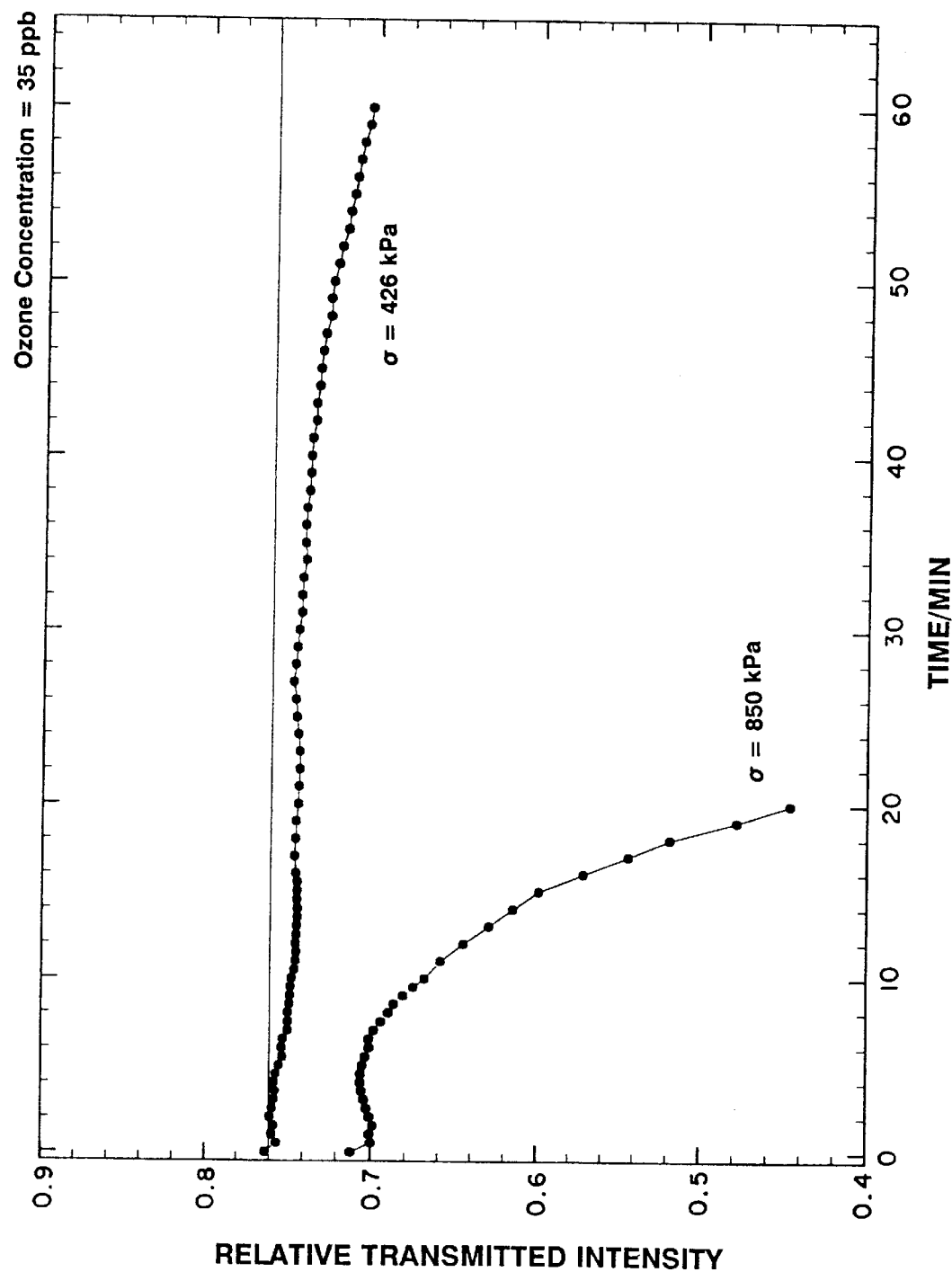
FIG. 5 is a graph of light intensity versus time for elastic films carried out at the same ozone concentration but at two different tensile stresses.
Figure 6:
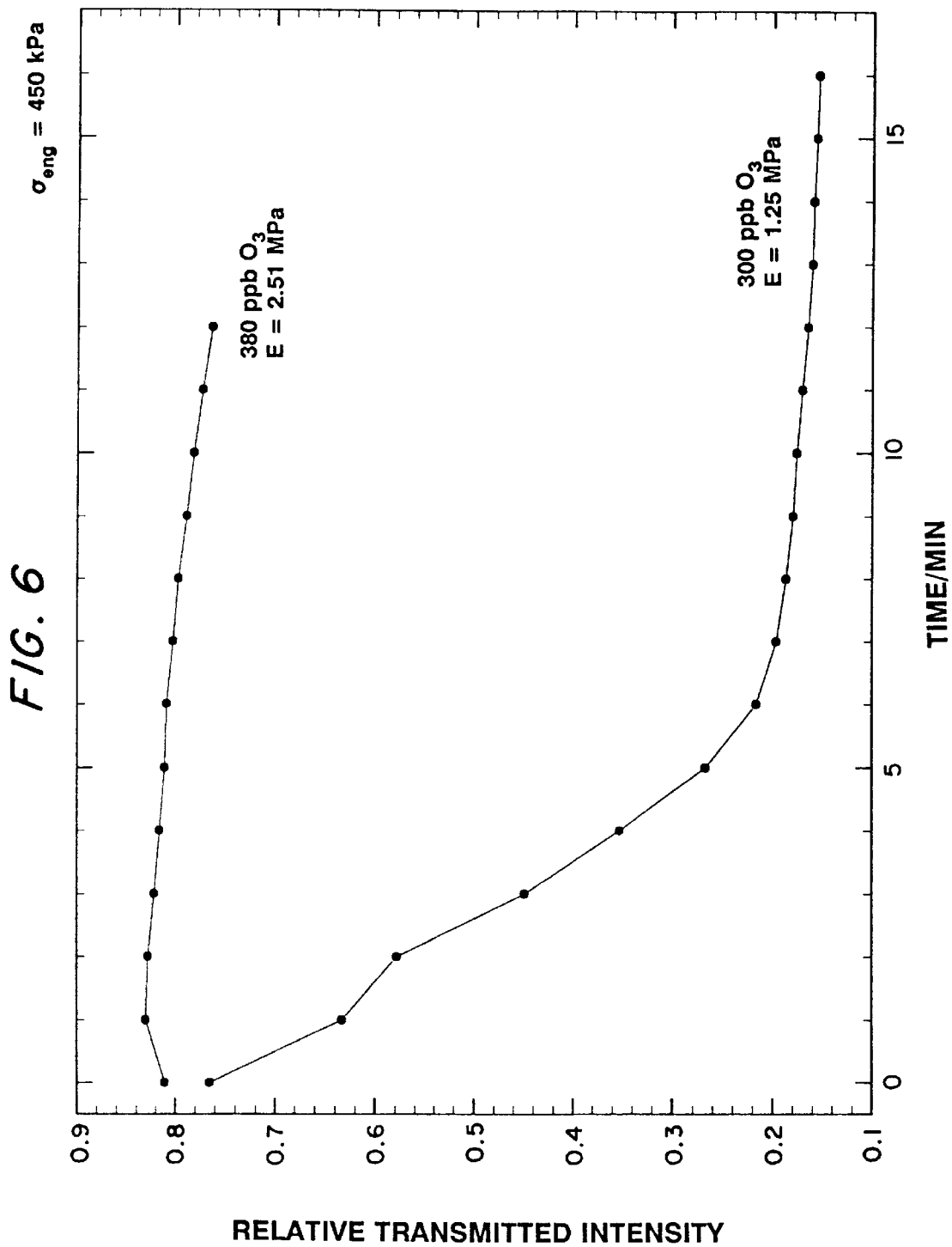
FIG. 6 is a graph of intensity versus time carried out at the same tensile stress and about the same ozone concentration but on two films having different Young's modulus.

Results of the experiments are illustrated in FIGS. 4, 5 and 6. FIG. 4 shows three plots of Time in minutes versus Relative Transmitted Intensity at a constant stress ($\sigma$) of 850 kPa (9,5600 $g/cm^2$) for three levels of ozone concentration in the chamber: 0.035 ppm (35 ppb), 0.08 ppm (80 ppb) and 0.3 ppm (300 ppb). Accuracy bf the ozone concentrations in the chamber is estimated to be ±20%. On this basis, it is estimated that there may be ±7 ppb error in the 35 ppb ozone concentration, ±16 ppb in the 80 ppb level and ±60 ppb in the 300 ppb level. The results demonstrate that as the ozone concentration was increased, the rate of loss of the relative transmitted light intensity, or the frosting rate, increased dramatically. The scatter of the data at very short times is attributed to inhomogeneities. Even at the lower ozone concentration of 35 ppb, the frosting rate was still appreciable, such that 50% of the initial light transmittance was observed after 18 minutes. This ozone concentration is about $\frac{1}{3}$ of the OSHA 8 hour average work limit of 100 ppb and is below ambient conditions present in most US cities on most summer days.

The effect on light intensity of increasing stress from 426 kPa (4,250 $g/cm^2$) to 850 kPa (8,500 $g/cm^2$) at constant ozone concentration of 35 ppb using samples I is given in FIG. 5. The figure shows that at the low stress of 426 kPa, the frosting rate was low but not zero and at the high stress of 850 kPa, the frosting rate increased dramatically. Thus, sensitivity of the sample film can be tuned to fit the needs of the situation; if a long term average is desired, the applied stress should be low, thereby increasing the effective life of the sample. If, on the other hand, a short term average is desired, the applied stress can be high in order to obtain a quick accurate reading of ozone concentration.

The effect of changing modulus E of the samples at constant engineering stress of 450 kPa (4,500 $g/cm^2$) and a nearly constant ozone concentration of 380 v. 300 ppb is shown in FIG. 6. The samples typically become less flexible on exposure to ozone. The modulus E of samples II was about one-half of samples I, i.e., 1.25 v. 2.51 Mpa, meaning that samples II were about twice as stiff as samples I. FIG. 6 shows that for the stiffer samples II, sensitivity to ozone decreased. For samples II, there remained a low but measurable loss of relative transmitted light intensity. Thus, if it is desired to adjust sensitivity over a wide range, beyond what can be provided by adjusting the stress, this can be achieved by changing to a sample with an appropriate modulus.

Modulus E, referred to herein is Young's Modulus which was determined by dividing the true stress $\sigma$ by the extension in the vicinity of 20% strain.

Reference herein is made to true stress and engineering stress. For purposes of clarification, true stress is the force or the weight applied to the sample divided by the stressed area of the sample whereas engineering stress is the force or the weight applied to the sample divided by the unstressed area of the sample.

EXAMPLE 2

This example demonstrates the use of elastic material of a non-uniform cross-sectional area but of a uniform thickness before stretching to determine ozone concentration.

As shown in FIG. 8, rubber elastic material 810 had uniform thickness but non-uniform cross-sectional area that was stretched. Rubber piece 810 shown in front view "A" had a trapezoidal shape with upper edge 812 that was 4 cm long, and lower edge 814 that was 1 cm long. Vertical distance between the upper and the lower edges was 6.5 cm. The upper and lower edges were parallel to each other. Thickness of rubber piece 810 was a uniform 0.15 cm from top to bottom.

Rubber piece 810 was clamped at its upper and lower edges and then stretched to 1.76 times its length to where its vertical distance was 11.26 cm. After stretching, the upper edge was still 4 cm, the lower edge was reduced to 0.5 cm, thickness of the rubber piece at its upper edge was still 0.15 cm and thickness at its lower edge was reduced to 0.10 cm.

The stretched rubber was then exposed to an air sample containing 200 ppb ozone and four photographs were taken, the first immediately and then at intervals of 4 minutes, 8 minutes, and 2 hours.

There was essentially no frosting in the first photograph. Frosting in the second photograph occurred at the lower or the third, where the rubber piece was thinnest. Frosting in the third photograph occurred at the lower half. Frosting in the fourth photograph occurred in the lowest $\frac{2}{3}$ of the rubber piece, indicating that frosting stopped at about that position and that further frosting would not take place if exposure to the ozone-containing environment continued. These photographs demonstrate a "front" of frosting proceeding upward from the thinnest portion of the trapezoidal rubber piece. The rate of advance of the front is proportional to the ozone concentration, which can be determined by the use of a calibration.

While presently preferred embodiments have been shown of the invention disclosed herein, persons skilled in this art will readily appreciate that various additional changes and modifications may be made without departing from the spirit of the invention as defined and differentiated by the following claims.

What is claimed is:

1. Ozone detector comprising stretched material which creates microcracks therein when exposed to ozone and a standard having a plurality of indicia which indicate ozone concentration based on integral intensity of light reflected or scattered from said material, cross-sectional area of said material is selected from the group consisting of uniform and non-uniform.

2. Ozone detector of claim 1 wherein said material is elastomeric.

3. Ozone detector of claim 1 wherein said material is selected from the group consisting of synthetic rubbers, natural rubbers, and mixtures thereof, and wherein said standard is a single support having a plurality of said indicia thereon which indicia are indicative of ozone concentration based on the relationship of increased degree of microcracking in said material representing greater ozone concentration.

4. Ozone detector comprising material which can create microcracks therein when exposed to ozone, thickness of said material is selected from the group consisting of uniform and non-uniform; means for stretching said material; a light source for projecting a light at said material in stretched condition; and means for detecting integral light intensity after it is reflected or scattered by said material wherein signal produced by the means for detecting is dependent on the presence of ozone in contact with said stretched material.

5. Ozone detector of claim 4 wherein said material is selected from the group consisting of synthetic rubbers, natural rubbers, and mixtures thereof.

6. Ozone detector of claim 4 comprising an enclosed chamber; said material disposed in said chamber; an opening in said chamber for said material to exit; and means for translating said material between said opening in said chamber and a point removed from said chamber.

7. Ozone detector of claim 6 including a converging lens which is adapted to receive the light reflected or scattered by said material and direct it to said light detecting means.

8. Ozone detector of claim 6 which includes means for collecting the reflected or scattered light.

9. Ozone detector of claim 8 wherein said material is in the form of an elongated film wound on a spool in said chamber and said opening in said chamber includes means for restricting air from entering into said chamber.

10. Ozone detector of claim 9 which includes a current amplifier connected to laid light detector and a voltmeter connected to said current amplifier.

11. Ozone detector of claim 10 including means for neutralizing ozone in said chamber so that it does not create microcracks in said material.

12. Ozone detector of claim 11 including a diverging lens for enlarging the light from said light source.

13. Ozone detector comprising an extended material of uniform thickness but of non-uniform width which creates microcracks when exposed to ozone and a standard having a plurality of indicia based on integral light reflected or scattered by said material indicating ozone concentration based on the relationship of increased degree of microcracking in said material representing a greater ozone concentration.

14. Ozone detector of claim 13 wherein said material is selected from the group consisting of natural rubbers, synthetic rubbers and mixtures thereof.

15. Ozone detector of claim 14 wherein said material is selected from the group consisting of polybutadiene, natural rubber, and mixtures thereof.

16. Method for detecting ozone concentration comprising the steps of (a) stretching a material, (b) exposing the material to a gaseous mixture containing ozone and allowing frosting of the material to take place based on formation of microcracks due to ozone in the gaseous mixture, (c) exposing the material to light, and (d) detecting ozone concentration in the gaseous mixture based on integral light reflected or scattered by the microcracks in the material, amount of microcracking is directly related to the ozone concentration in the gaseous mixture.

17. Method of claim 16 wherein the gaseous mixture contains ozone in approximate concentration of 0.001–1 ppm and the material is selected from the group consisting of synthetic rubbers, natural rubbers, and mixtures thereof.

18. Method of claim 17 wherein said step of exposing the material to light is accomplished by projecting a light emanating from a light source.

19. Method of claim 18 including the step of converging the light reflected or scattered by the material.

20. Method of claim 19 wherein the material is selected from the group consisting of polybutadiene, natural rubber, and mixtures thereof.

* * * * *